Figure 1:
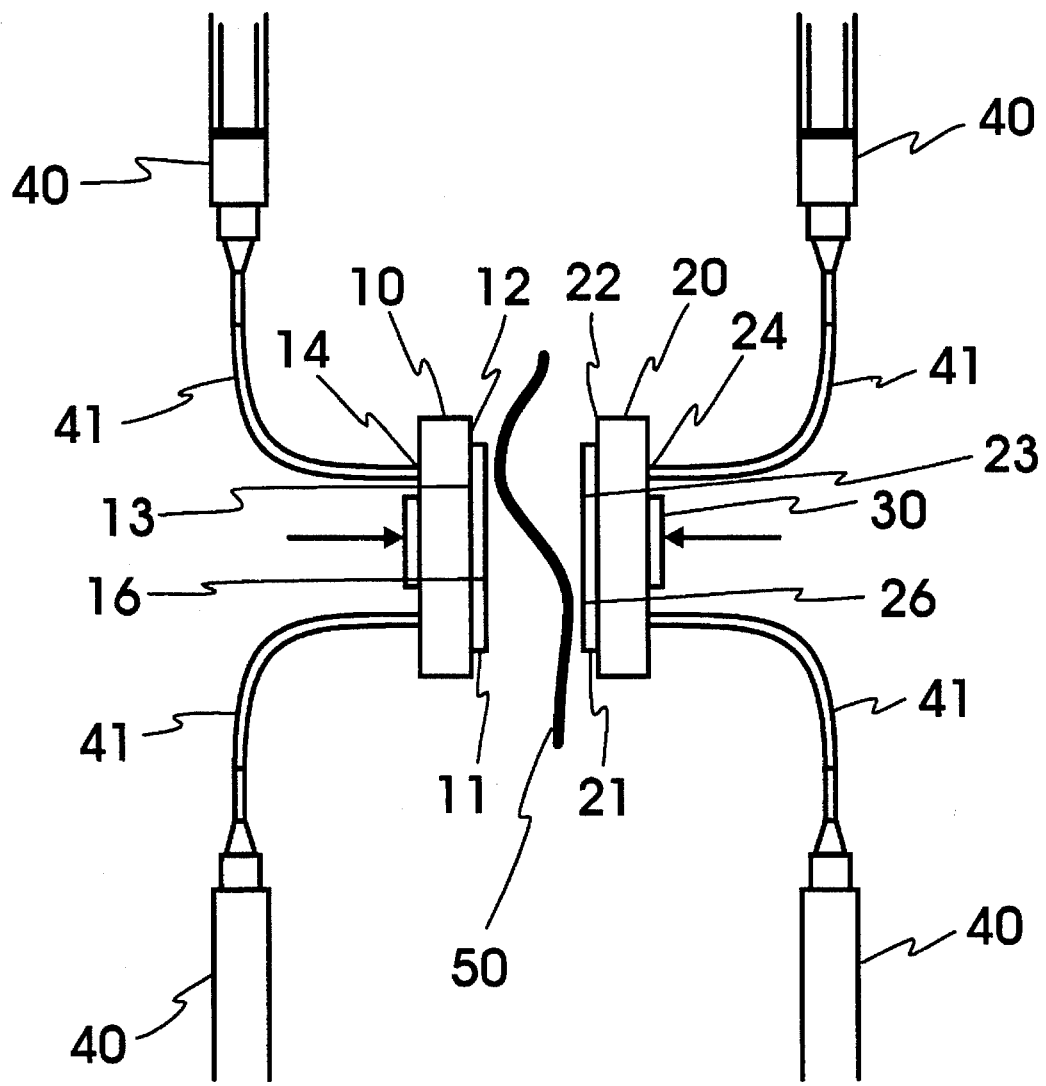

United States Patent [19]

Carlton

[11] Patent Number: 5,503,005

[45] Date of Patent: Apr. 2, 1996

[54] DUAL SIDE PLANT LEAF WASHER AND IMMERSION CELL

[75] Inventor: James B. Carlton, College Station, Tex.

[73] Assignee: The United States of America as represented by the Secretary of Agriculture, Washington, D.C.

[21] Appl. No.: 303,808

[22] Filed: Sep. 9, 1994

[51] Int. Cl.$^6$ ....................................................... G01N 33/00
[52] U.S. Cl. ........................... 73/61.62; 73/866; 73/432.1
[58] Field of Search ............................... 73/61.62, 61.41, 73/432.1, 866

[56] References Cited

U.S. PATENT DOCUMENTS 4,493,815  1/1985  Fernwood et al. ..................... 422/101

FOREIGN PATENT DOCUMENTS 332902  12/1993  Japan ..................... 73/866

OTHER PUBLICATIONS

Franz, Thomas J., "Percutaneous Absorption, On The Relevance of In Vitro Data", *The Journal of Investigative Dermatology*, Mar. 1975, vol. 64, No. 3, pp. 190–195.
Franz Diffusion Cells and Apparatus, Crown Glass Company.

Primary Examiner—Hezron E. Williams
Assistant Examiner—Daniel S. Larkin
Attorney, Agent, or Firm—M. Howard Silverstein; Randall E. Deck; John D. Fado

[57] ABSTRACT

An apparatus and method for measuring agricultural spray deposits and maximum liquid formulation retention on plant leaf surfaces are disclosed. The apparatus includes a first chamber having an annular seal mounted thereon which defines a first cavity, and a second separable chamber also having an annular seal thereon defining a second cavity. Each chamber also includes at least one access port communicating with that chamber's respective cavity, and are aligned with their annular seals juxtaposed in an opposable relationship. Releasable force application means are also provided for forcing the chambers together with the seals in an abutting relationship. In use, a leaf of the target plant is inserted between the annular seals and the chambers are forced together, retaining the leaf between the seals and forming first and second accessible compartments defined by the leaf and the cavities of the first and second chambers, respectively. Test liquid, such as an agricultural spray of interest or a solvent for spray residues, may then be applied into one or both compartments through the access ports to selectively contact the upper or lower leaf surface. Following contact with the appropriate leaf surface, the liquid may be recovered and assayed to determine the volume of liquid retained on the leaf surface, or for the presence or amount of agricultural spray deposits on the leaf.

22 Claims, 6 Drawing Sheets

5,503,005

DUAL SIDE PLANT LEAF WASHER AND IMMERSION CELL

BACKGROUND OF THE INVENTION

1. Field of the Invention

The invention relates to a method and apparatus for facilitating the measurement of agricultural spray deposits and spray retention on plant leaves.

2. Description of the Prior Art

Application of agricultural chemicals by aerial and ground spraying has long been prevalent in the U.S. and worldwide. However, lack of accurate information regarding the retention of sprays on plant surfaces and existing residue levels, could lead to excessive or insufficient field application or sub-optimal application protocols, ultimately resulting in increased expenses to the user or possible contamination of the environment.

Although artificial spray sampling collectors may be used, such devices typically suffer from the inherent disadvantage of disturbing the sampling environment to such an extent that extrapolating data to predict spray deposition on target plants is uncertain. Ware et al. (1975, J. Economic Entomology, 68:549–550) proposed avoiding this uncertainty by sampling actual target surfaces to determine the gross deposit quantity. Briefly, field sprayed cotton stalks were cut and immersed in their entirety in a large solvent bath. Samples from the bath were later analyzed for DDT content. More recently, Carlton and Bouse (1988, Trans. ASAE, 31:990–997) disclosed a cylindrical collector for sampling aerial sprays. In spite of these developments there remains a persistent need for simple methods or devices to facilitate the measurement of agricultural spray deposits and spray retention on plant leaves.

SUMMARY OF THE INVENTION

We have now invented an apparatus and method for measuring agricultural spray deposits and spray retention on plant leaf surfaces. The apparatus includes first and second separable chambers or test cells each having an open cavity on one end which is defined by an annular seal mounted on the exterior thereof. The two chambers are aligned with their annular seals juxtaposed in an opposable relationship, such that they abut when the chambers are forced together by a releasable force application means. The cavities may be independently accessed through at least one port provided in each chamber.

In use, a leaf of the target plant is inserted between the chambers, which are then forced together to sealably retain the leaf between the seals and form first and second accessible compartments defined by the leaf and the respective adjacent cavity. Test liquid, such as an agricultural spray of interest or a solvent for spray residues, may then be applied into one or both compartments through the access ports to selectively contact the upper or lower leaf surface. Following contact with the appropriate leaf surface, the liquid may be recovered and assayed to determine the volume retained on the leaf surface, as in the case of using agricultural spray formulations as the test liquid. Alternatively, the assay may determine the presence or amount of agricultural spray deposits or other residues on the leaf which may be recovered when using a solvent as the test liquid.

In accordance with this invention, it is an object to provide a simple and inexpensive apparatus and method for measuring agricultural spray deposits and spray retention on plant leaf surfaces.

It is another object of this invention to provide an apparatus and method for selectively measuring agricultural spray deposits and spray retention on either or both of the top or bottom surface of a plant leaf. The invention thereby allows a user in the field to sample spray deposition and determine if the spray formulation or application protocol are suitable, that is, applying an effective amount to a target leaf surface and if the spray is being retained, or if the formulation or application protocol are insufficient or excessive. Using the invention the user may also determine the presence or amount of preexisting spray residues and hence the need for further application. Further still, the determination of preferential spray retention on various leaf surfaces using the invention could lead to reduction of application rate by improving or designing spray formulations for higher retention, and by improving upon application protocols or equipment design.

Other objects and advantages of the invention will become readily apparent from the ensuing description.

BRIEF DESCRIPTION OF THE DRAWINGS

FIG. 1 is a side view of a first embodiment of the apparatus of the invention in an open position to receive a plant leaf and having closed first and second chambers each provided with a pair of access FIG. 2 is a cross section of one chamber of the device shown in FIG. 1.

FIG. 3 is a end view of one chamber of the device shown in FIG. 1.

FIG. 4 is a cross section of an alternative chamber of the device having a recessed cavity.

FIG. 5 is a side view of a second embodiment of the apparatus of the invention wherein the access ports are formed by opposite open ends of the chambers.

FIG. 6 is a cross section of one chamber of the device shown in FIG. 5.

DETAILED DESCRIPTION OF THE INVENTION

The apparatus of this invention was designed for the measurement of the deposit or retention of a variety of formulations of agricultural agents applied onto plant leaves. Without being limited thereto, the device is particularly suited to the measurement of any agricultural agents applied by aerial or ground spraying, or other ground based application or irrigation methods, especially formulations of commercial chemical or biological pesticides, herbicides, fungicides, insecticides and fertilizers. The device may also be used to measure spray deposit or retention on the leaves of virtually any broad leaf plant of interest, particularly agronomically important field crops, vegetables, fruits and fruit Referring now to FIGS. 1 and 2, the apparatus 1 includes first and second chambers or housing members 10 and 20, respectively. The first chamber 10 includes an annular seal or gasket 11 mounted on an exterior surface 12, with the inner surface of the annulus delineating a cavity 13. At least one access port or aperture 14 is provided through the chamber 10 communicating with cavity 13 to allow addition and removal of test liquids. Second chamber 20 is similarly constructed, having annular seal 21 on surface 22, cavity 23, and access ports 24. It is understood that the second chamber 20 need not be identical to the first chamber 10.

Figure 2:
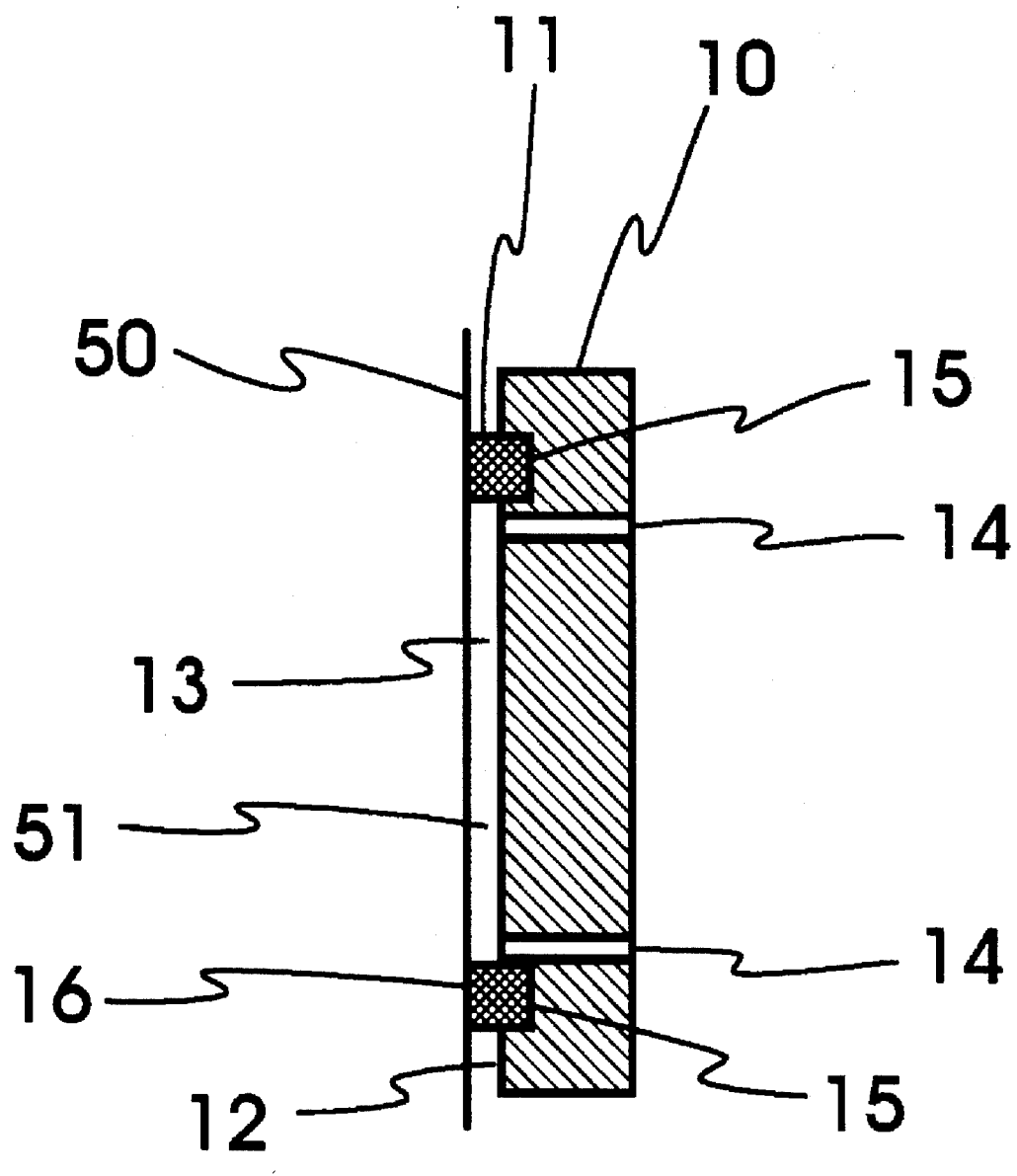

Chambers 10 and 20 may take virtually any shape, although cylindrical chambers are preferred for ease of construction. Regardless of the shape selected, the exterior surfaces 12 and 22 on which the seals are attached should be planar to enhance the formation of a watertight junction between the surface and the seal as well as between the seal and the leaf during use. Optional dove-tailed grooves 15 (FIG. 2, only one shown) may also be provided on the surfaces, into which the seals may be press fit for improved adherence and leakage prevention.

Figure 3:
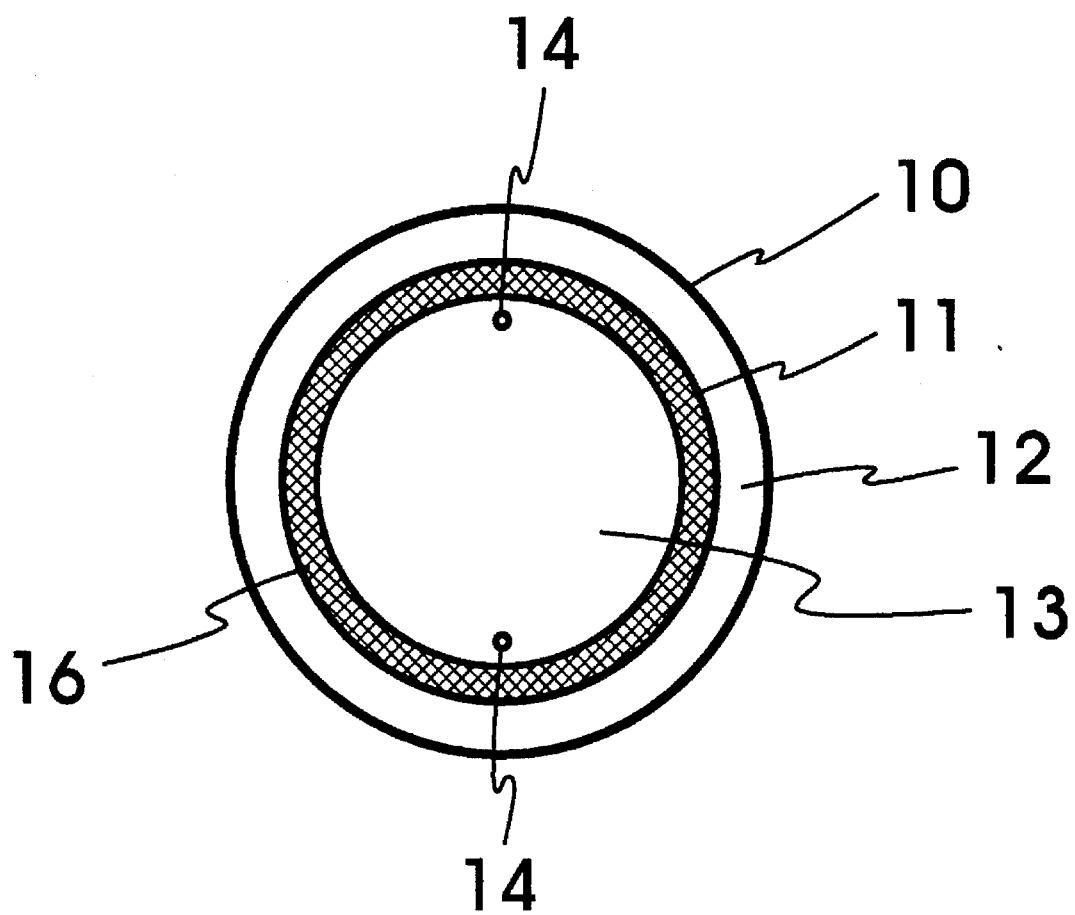
Figure 4:
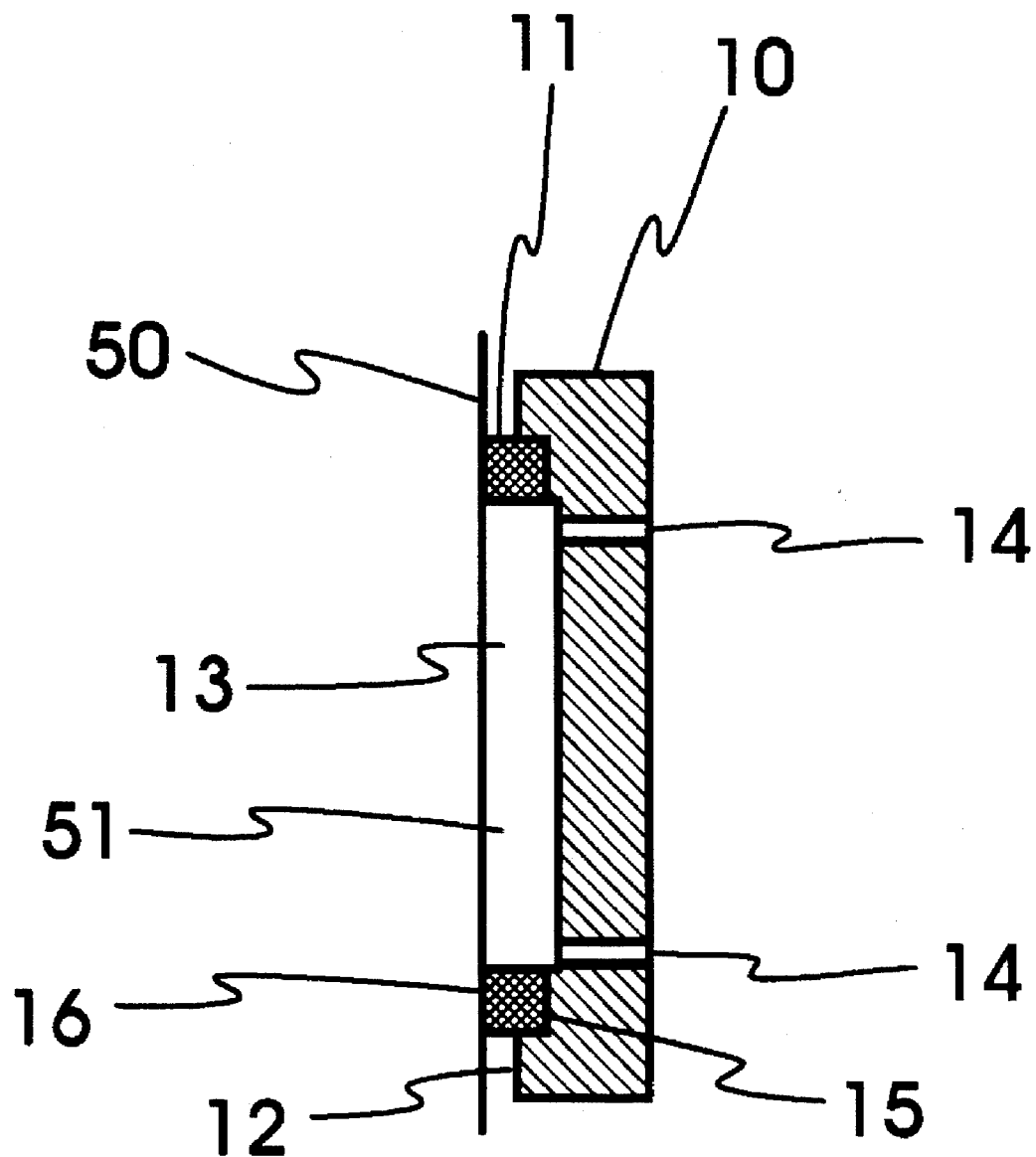
Figure 6:
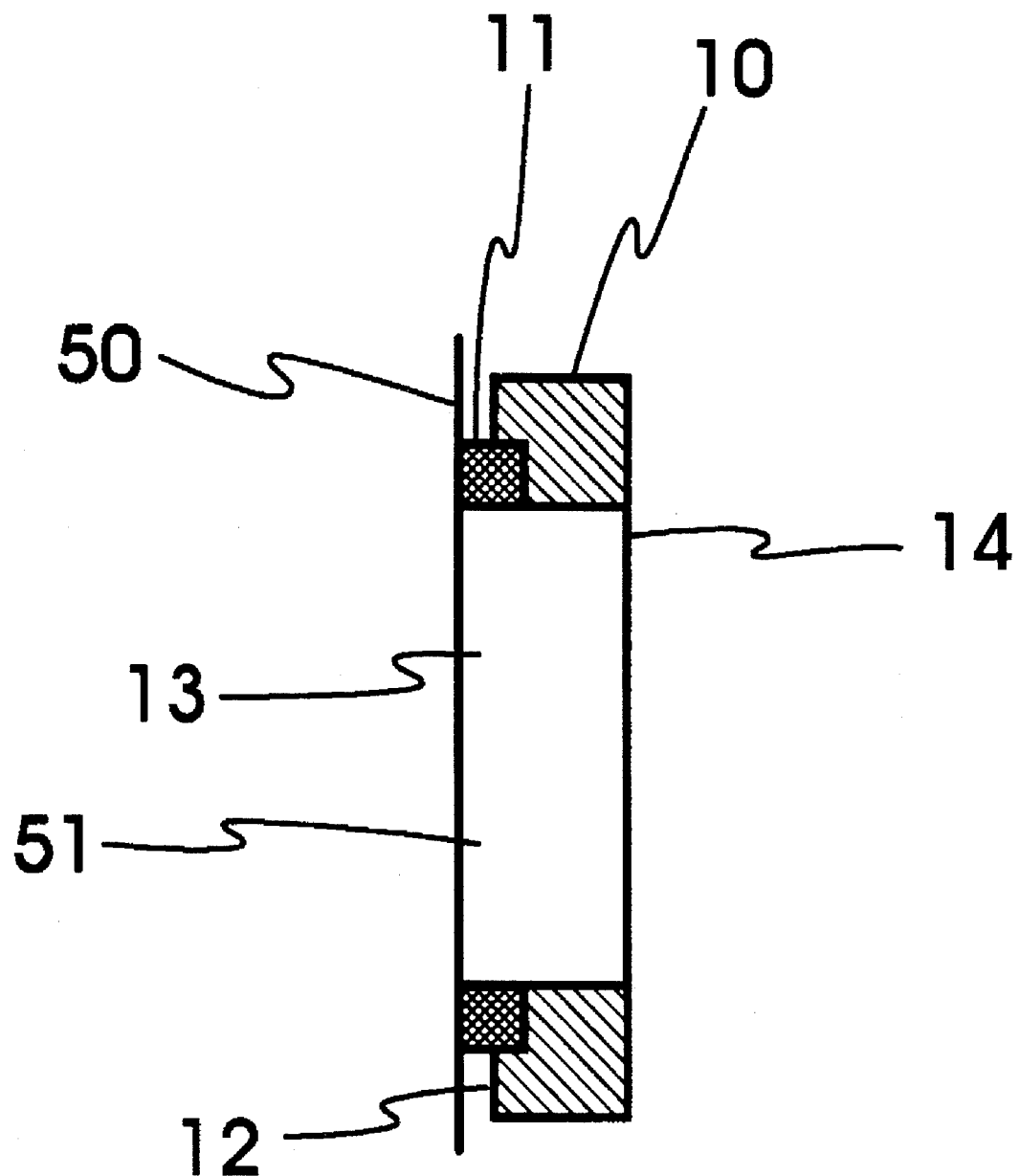

The size and shape of the cavities 13 and 23 also are not critical and may vary with the volume of the test liquid to be used and the size and shape of the target leaf. Although a variety of shapes may be used, cavities having a circular cross section as shown in FIG. 3 are preferred for simplicity and to facilitate removal of the test solutions. The width or diameter of the cavity, and hence that of the seals 11 and 21 as well, should be sufficient to accommodate a statistically significant area of the target leaf surface for contact with the test solutions, while securing the leaf between the seals without leakage between the cavities. The depth of the cavity is also variable and may be selected to accommodate the volume of test liquid to be applied onto the target leaf. In one preferred embodiment shown in FIG. 2, the depth of the cavity is merely the height of the seal above the chamber surface. Alternatively, as shown in FIG. 6 the cavities 13 and 23 may extend through the chambers 10 and 20, in which event the access ports 14 and 24 may be merely open ends of the respective chambers. The skilled practitioner will understand that cavities of intermediate depth, extending only partially through the chamkers as shown in FIG. 4, may also be constructed. Without being limited thereto, the cavity and seal inside diameters may vary between about 1 cm to 10 cm, preferably between about 1 to 8 cm, while the cavity depth should be at least 0.5 mm, and may preferably vary between about 0.5 mm to 10 mm, particularly between about 1 to 3 mm.

Figure 5:
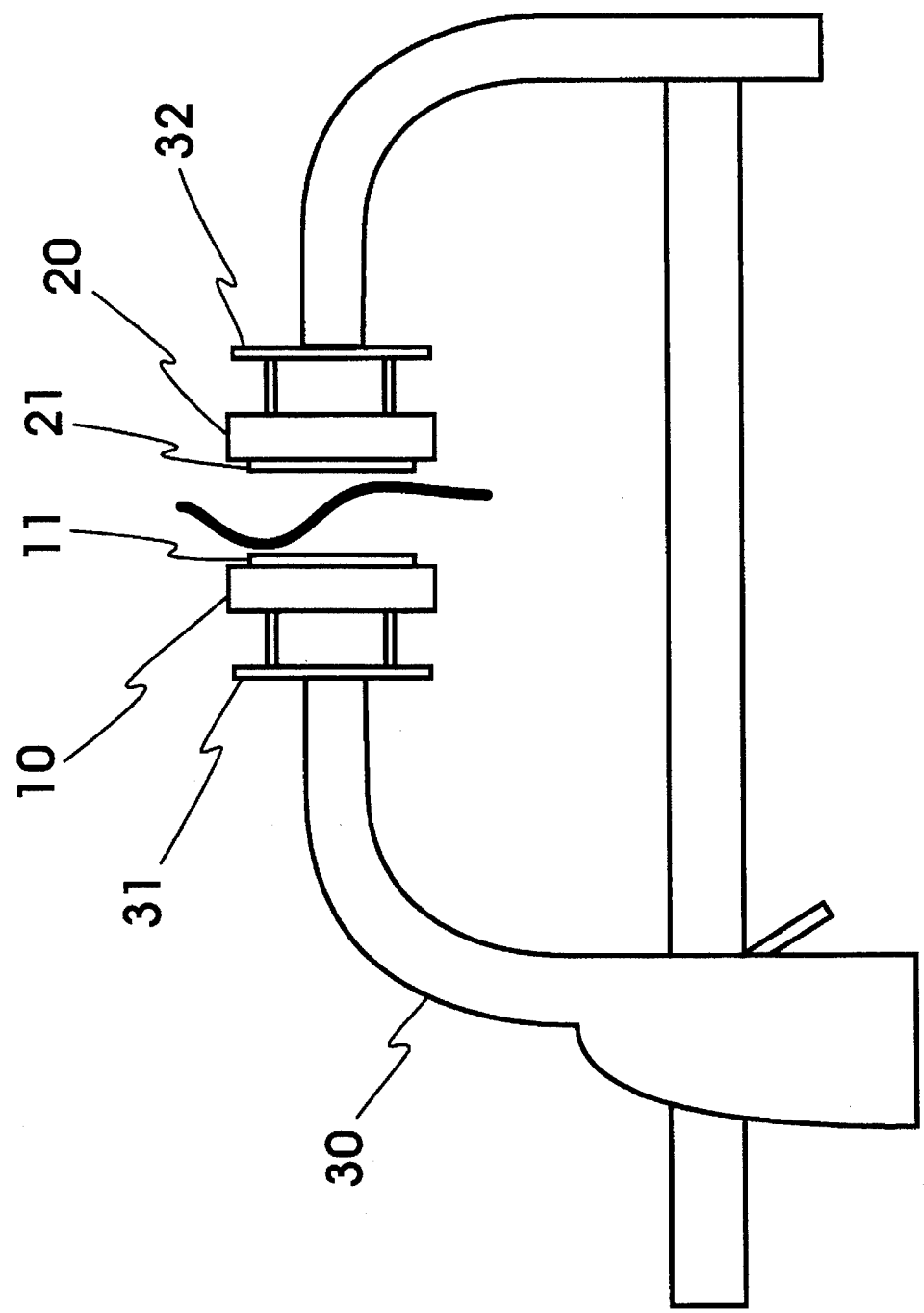

Chambers 10 and 20 are mounted onto a releasable force application means 30, which has the dual function of supporting the chambers in an opposed relationship, as well as applying butt sealing pressure (in the direction of the arrows in FIG. 1) to force and secure the chambers together. In the preferred embodiment, the force application means comprises a clamp which provides a compressive force between its jaws, to which the chambers are directly or indirectly mounted. A plurality of hand-held clamps may be used, including spring-loaded clamps, bar clamps and pipe clamps. As shown in FIG. 5, the chambers 10 and 20 are mounted to the jaws 31 and 32 of a conventional bar clamp. Bar and pipe clamps are particularly preferred, allowing the pressure or force applied to the chambers to be varied to prevent damage to the target leaf. In the alternative to clamps, the practitioner skilled in the art will recognize that a variety of other force application means may be used, including but not limited to screws joining and extending through both chambers or frame plates or flanges attached to the chambers, or springs, belts or elastic cords. Regardless of the device selected, the force application means should be capable of applying sufficient force to effectively form watertight junctions between the annular seals 11 and 21 and a leaf inserted therebetween. This may vary with the particular annular seals used, the test liquid or solvents, or target leaf. However, without being limited thereto, preferred clamps should be capable of applying a compressive force of about 100N onto the surfaces of the seals.

When mounted onto the force application means 30, chambers 10 and 20 should be positioned or aligned in an opposable relationship, with annular seals 11 and 21 being juxtaposed. Thus, when force is applied to bring the chambers together, the opposed surfaces 16 and 26 of seals 11 and 21 should concentrically abut one another. To prevent compression of the seals or their adhesion to one another during storage, particularly when using a spring loaded clamp as the force application means, the jaws of the clamp may be blocked open, for example, with a piece of wood.

Annular seals 11 and 21 are necessarily substantially the same size and shape such that they abut with alignment when the chambers 10 and 21 are forced together. This allows a leaf to be held flat between the seals while maximizing the leaf and seal contact area and minimizing stretching or shearing forces which may tear the leaf. Moreover, in the preferred embodiment, the annular seals are constructed from resilient or compliant polymeric or rubber material and have flat or planar contact surfaces 16 and 26 with a relatively large area, to avoid cutting the leaf when force is applied by means 30, but still form watertight seals with the leaf. It is understood that any material selected should be compatible with any solvents or agronomic carriers in the test liquids of interest, such as water, acetone, lower alcohols, methyl ethyl ketone or soap solutions. Without being limited thereto, preferred seals include piston seals and shaft-cylinder seals of ethylene-propylene (EPR). Also preferred are those seals having flat contact surfaces 16 and 26 at least about 3 mm wide (the difference between the inside and outside diameters). Although it is envisioned that conventional O-rings may be used with some leaves which are relatively strong, generally they are not preferred because their small contact surface may cut the leaves from lateral or side slipping when force is applied by means 30.

The chambers 10 and 20 may also be constructed from a variety of different materials. Preferred materials include but are not limited to non-water-wettable or hydrophobic materials, plastics, stainless steel, and particularly TEFLON and polyethylene. As with the annular seals, the material selected should be compatible with any solvents or agronomic carriers anticipated for use in the test liquids.

As shown in the embodiment of FIG. 1, optional syringes 40 may be provided for addition and removal of test liquids through each of the access ports 14 and 24. The syringes may communicate directly or, as shown in the Figure, indirectly with the access ports via lines or tubes 41. For added convenience when handling, the syringes may be removably attached to the chambers or onto the clamp or other force application means 30.

Collection of samples from plant leaves for the measurement of deposition and retention of agricultural chemical formulations may be readily performed using the device of this invention. In accordance with a first embodiment, a leaf 50 from a plant which has been treated with a formulation of an active agent of interest, including but not limited to spray, dust or granular formulations, is collected and positioned between chambers 10 and 20 such that it covers the entire area circumscribed by the seals 11 and 21. Leaves having large ribs, veins or folds should be avoided, or these structures should not be positioned across the seals, to minimize subsequent leakage. The chambers are then firmly pressed together by force application means 30, forming first and second accessible compartments 51 (FIG. 2, only one shown) which are separated by the leaf 50 and defined by first and second cavities 13 and 23, respectively. Formation of watertight seals between the leaf and seals 11 and 21 may be aided by application of a small amount of an optional sealant, such as VASELINE or petroleum jelly, onto the adjacent contact surfaces 16 and 26. Thus, the surfaces of the leaf are in communication with compartments 51, and may be selectively accessed through the ports 14 and 24. A test liquid, comprising a with solvent for the formulation or active agent, may then be introduced into either or both compartments through the access ports, to separately contact the leaf surfaces and remove any deposits therefrom. Removal of leaf deposits may be enhanced by gentle agitation. When using a device as in FIG. 1, to avoid leaf damage the test liquid is preferably pulled into compartment 51 from a first syringe 40 by suction applied through the second syringe communicating with the compartment. Also, agitation may be effected by alternately withdrawing and reinjecting the liquid through the lower piston-equipped syringes 40. Following contact with the leaf, the test liquid may be finally recovered by withdrawal through the lower syringes 40, or by decantation or aspiration with a vacuum device from the apparatus of FIG. 5. The recovered test liquid may then be analyzed using conventional procedures, such as gas chromatography or NMR spectroscopy, to detect and/or quantitatively determine the presence and amount of the active agent on the sampled are of each leaf surface. It is understood that the leaf surfaces may be assayed simultaneously (as with the device of FIG. 1) or consecutively (as with the device of FIG. 5), although simultaneous analyses requires that access ports 14 and 24 be closed to prevent spillage.

Alternatively, rather than assaying the active agent, an inert tracer such as a conventional dye or fluorescent marker may be incorporated into the formulation of interest prior to application onto the plant. The test liquid recovered following washing of the leaf may then be assayed for the tracer. Appropriate techniques for tracer assay may be readily determined by the practitioner skilled in the art and include simple visual assessment when only qualitative results are required, or colorimetric or fluorometric analysis for quantitative measurements. Without being limited thereto, FD & C #1 blue dye (Warner Jenkinsen Co., St. Louis, Mo.) is a preferred tracer, absorbing light at 620 nm. For aerial spray applications, formulations of 38 l/ha water containing 100 g/ha FD & C #1 dye plus 114 ml/ha of X-100 surfactant have been adequate.

Measurement of the recovered active agent or tracer permits evaluation of the penetration of the formulation into the plant canopy, its deposition onto the top and bottom surfaces of the plant leaves, as well as the concentration or amount of formulation retained on the leaf surfaces. This in turn allows the user to evaluate the adequacy of the formulation and/or application technique for their desired result.

The same technique may also be used to determine the presence of pre-existing residues of agricultural chemicals on plant leaves. Plant leaves from suspect plants may be collected and sampled using an appropriate solvent as described hereinabove. The rinsate may then be analyzed to detect and/or quantitatively determine the presence and amount of any active agent of interest on the sampled leaf area.

In an alternate embodiment, determination of the retention of a particular formulation of an agricultural chemical on a leaf may be performed without the need for the multiple steps of contacting with the formulation followed by wash solvent as described in the preceding embodiment. According to this method, a leaf from a target plant is secured between chambers 10 and 20, and a known volumetric sample of a subject liquid formulation is directly introduced into either or both cavities 13 and 23 through the access ports 14 and 24 to contact the surfaces of the leaf. Free or non-bound liquid formulation may then be recovered as described hereinabove. While liquid volume retention may be determined from measurements performed on a single leaf, to minimize errors, the process is repeated on a plurality of different leaves, with the liquid recovered from the first leaf applied onto the same surface (top or bottom) of succeeding leaves. Regardless of the number of leaves used, the volume of liquid formulation retained by the leaf surface, referred to as the maximum retention volume or capacity, is then the difference between the volume of liquid recovered from the last leaf and that originally applied to wet the first leaf. Retention may also be expressed in terms of the volume retained per unit area of the leaf surface (top and/or bottom) since the total contact area of the leaf or leaves is known. Using the measured retention capacity of the leaves of a target plant, and particularly any preferential retention by the upper vs. lower surface, spray formulations or application techniques may be improved as needed.

It is understood that the foregoing detailed description is given merely by way of example and that modifications and variations may be made therein without departing from the spirit and scope of the invention.

I claim:

1. An apparatus for measuring agricultural spray deposit and liquid formulation retention on plant leaf surfaces comprising:

a. a first chamber having an annular seal mounted thereon defining a first cavity, said first chamber further including at least one access port communicating with said first cavity;

b. a second chamber separable from said first chamber, said second chamber having an annular seal mounted thereon defining a second cavity, said second chamber further including at least one access port communicating with said second cavity, wherein said first and second chambers are positioned with said annular seals juxtaposed in an opposable relationship;

c. releasable force application means for supporting said first and second chambers in an opposed relationship and forcing said first and second chambers together with said annular seals in an abutting relationship;

wherein a plant leaf may be secured between said annular seals, forming a first accessible compartment defined by said first cavity and one surface of said leaf, and a second accessible compartment defined by said second cavity and the opposite side of said leaf, and said annular seals are constructed from a material effective for sealably retaining a plant leaf therebetween without tearing said leaf.

2. An apparatus as described in claim 1 wherein said first and second chambers are substantially cylindrical, and said annular seals are mounted on one end of each cylinder.

3. An apparatus as described in claim 2 wherein said cylindrical chambers are hollow and said access ports comprise an open end of said cylindrical chambers opposite from said end to which said annular seals are mounted.

4. An apparatus as described in claim 2 wherein each of said first and second chambers have at least two of said access ports.

5. An apparatus as described in claim 4 further comprising syringes communicating with each of said access ports.

6. An apparatus as described in claim 2 wherein said first and second chambers are substantially identical.

7. An apparatus as described in claim 1 wherein said annular seals are flat ethylene-propylene rings.

8. An apparatus as described in claim 1 wherein said first and second chambers are formed from TEFLON.

9. An apparatus as described in claim 1 wherein said releasable force application means comprises a clamp.

10. A method for measuring the retention or deposition of agricultural spray material on the surfaces of plant leafs comprising:

a. providing an apparatus comprise:
    1. a first chamber having an annular seal mounted thereon defining a first cavity, said first chamber further including at least one access port communicating with said first cavity;
    2. a second chamber separable from said first chamber, said second chamber having an annular seal mounted thereon defining a second cavity, said second chamber further including at least one access port communicating with said second cavity, wherein said first and second chambers are positioned with said annular seals juxtaposed in an opposable relationship, and;
    2. releasable force application means for supporting said first and second chambers in an opposed relationship and releasably forcing said first and second chambers together with said annular seals in an abutting relationship;
and wherein said annular seals are constructed from a material effective for sealably retaining a plant leaf therebetween without tearing said leaf;

b. inserting a plant leaf between said annular seals, and forcing said first and second chambers together with said force application means to secure said leaf between said annular seals and form a first accessible compartment defined by said first cavity and one surface of said leaf, and a second accessible compartment defined by said second cavity and the opposite side of said leaf;

c. applying a test liquid into said first compartment through said access port of said first chamber to allow said liquid to contact one surface of said leaf;

d. recovering said test liquid from said first compartment through said access port of said first chamber;

e. assaying said test liquid recovered from said first compartment to determine either the volume of liquid retained on said leaf, or the presence or amount of agricultural chemicals from said leaf.

11. The method as described in claim 10 further comprising:

f. applying test liquid into said second compartment to allow said liquid to contact the other surface of said leaf;

g. recovering said test liquid from said second compartment;

h. assaying said liquid recovered from said second compartment to determine the volume of liquid retained on said leaf or the presence or amount of agricultural chemicals from said leaf.

12. The method as described in claim 10 wherein said liquid is a solvent and the step of assaying comprises determining the presence or amount of agricultural chemicals from said leaf.

13. The method as described in claim 12 further comprising the initial step of spraying an agricultural agent onto said leaf.

14. The method as described in claim 10 wherein said liquid comprises an agricultural spray and the step of assaying comprises determining the volume of said liquid retained on said leaf.

15. A method as described in claim 10 wherein said first and second chambers are substantially cylindrical, and said annular seals are mounted on one end of each cylinder.

16. A method as described in claim 15 wherein said cylindrical chambers are hollow and said access ports comprise an open end of said cylindrical chambers opposite from said end to which said annular seals are mounted.

17. A method as described in claim 15 wherein each of said first and second chambers have at least two of said access ports.

18. A method as described in claim 17 further comprising syringes communicating with each of said access ports.

19. A method as described in claim 15 wherein said first and second chambers are substantially identical.

20. A method as described in claim 10 wherein said annular seals are flat ethylene-propylene rings.

21. A method as described in claim 10 wherein said first and second chambers are formed from TEFLON.

22. A method as described in claim 10 wherein said releasable force application means comprises a clamp.

* * * * *